(12) United States Patent
Lesch et al.

US010829785B2

(10) Patent No.: US 10,829,785 B2
(45) Date of Patent: Nov. 10, 2020

(54) NUCLEIC ACID APPLICATION PRIMERS

(71) Applicant: Trizell Ltd., Chinnor (GB)

(72) Inventors: Hanna P. Lesch, Kuopio (FI); Kari J. Airenne, Kuopio (FI); Seppo Yla-Herttuala, Kuopio (FI)

(73) Assignee: Trizell Limited, Chinnor (GB)

( * ) Notice: Subject to any disclaimer, the term of this patent is extended or adjusted under 35 U.S.C. 154(b) by 0 days.

(21) Appl. No.: 16/681,964

(22) Filed: Nov. 13, 2019

(65) Prior Publication Data

US 2020/0071725 A1    Mar. 5, 2020

Related U.S. Application Data

(62) Division of application No. 12/522,646, filed as application No. PCT/GB2008/000464 on Feb. 11, 2008, now abandoned.

(30) Foreign Application Priority Data

Feb. 12, 2007   (GB) .................................. 0702695.8

(51) Int. Cl.
| | |
|---|---|
| *C07H 21/04* | (2006.01) |
| *C12N 15/00* | (2006.01) |
| *C12N 15/63* | (2006.01) |
| *A61K 48/00* | (2006.01) |
| *C12N 15/86* | (2006.01) |
| *C07K 14/005* | (2006.01) |
| *C12N 7/00* | (2006.01) |

(52) U.S. Cl.
CPC .......... *C12N 15/86* (2013.01); *A61K 48/0091* (2013.01); *C07K 14/005* (2013.01); *C12N 7/00* (2013.01); *A61K 48/00* (2013.01); *C12N 2710/14021* (2013.01); *C12N 2710/14043* (2013.01); *C12N 2710/14051* (2013.01); *C12N 2740/15043* (2013.01); *C12N 2740/15051* (2013.01); *C12N 2740/16022* (2013.01); *C12N 2740/16043* (2013.01); *C12N 2740/16045* (2013.01); *C12N 2740/16051* (2013.01); *C12N 2810/6081* (2013.01)

(58) Field of Classification Search
CPC . C12N 15/86; C12N 7/00; C12N 2710/14051
See application file for complete search history.

(56) References Cited

U.S. PATENT DOCUMENTS 7,250,299 B1 *  7/2007  Naldini et al.

OTHER PUBLICATIONS

Dull et al. A third-generation lentivirus vector with a conditional packaging system. J. Virol. 72:8463-8471, (Year: 1998).*
Mitta et al. Advanced modular self-inactivating lentiviral expression vectors for multigene interventions in mammalian cells and in vivo transduction. Nucleic Acids Research 30: e113, 18 pages, (Year: 2002).*

* cited by examiner

*Primary Examiner* — Quang Nguyen
(74) *Attorney, Agent, or Firm* — Pharmaceutical Patent Atty's LLC

(57) ABSTRACT

Novel forward primer, reverse primer and poly-linker suitable for replication of nucleic acids in e.g., 293 cells.

4 Claims, 2 Drawing Sheets

Specification includes a Sequence Listing.

NUCLEIC ACID APPLICATION PRIMERS

CROSS REFERENCE TO RELATED APPLICATIONS

This application is a Divisional of co-pending U.S. Ser. No. 12/522,646 filed 9 Jul. 2009, which is a National Stage entry of and asserts priority to PCT Application Serial No. PCT/GB2008/000464 filed 11 Feb. 2008, which in turn asserts priority from Great Britain patent filing Serial No. GB07/02695.8 filed 12 Feb. 2007, the contents of which are here incorporated by reference.

GOVERNMENT INTEREST

None

FIELD OF THE INVENTION

The invention relates to methods for the production of lentiviral vectors.

REFERENCE TO A "SEQUENCE LISTING"

SEQ ID NO 1 provides the sequence of Artificial Sequence DNA. SEQ ID NO 2 provides the sequence of Artificial Sequence DNA. SEQ ID NO 3 provides the sequence of Artificial Sequence DNA.

BACKGROUND OF THE INVENTION

Lentiviruses, such as Human Immunodeficiency Virus I, are promising tools for gene therapy due to their ability to transduce and integrate into the genome of both dividing and non-dividing cells. However, the production of replication-defective lentiviral vectors for large-scale clinical use is challenging. Lentiviral vectors are normally produced by cotransfecting 293T human embryonic kidney cells with several different plasmid constructs. The first clinical lentiviral vector production was based on a two-plasmid system (Lu et al., 2004). To further improve the safety of the system, lentivirus genome can be separated into four plasmids. The plasmids are a self-inactivating transfer vector; a packaging plasmid containing gag-pol; a rev plasmid; and an envelope glycoprotein plasmid which usually encodes vesicular stomatitis virus glycoprotein G (VSV-G). To upscale lentivirus production, the growth of adherent cells has been changed to cell factories. Lentiviral vectors have also been transiently produced in suspension cultures using 3-L bioreactors in serum-free conditions.

As transient transfection systems for virus production can be problematic and time-consuming, attempts have been made to develop stable large-scale production systems. However, the toxicity of lentiviral protease and the fusogenic envelope protein, VSV-G, has prohibited constitutive vector production. One production method uses inducible packaging cell lines, controlled either by tetracycline- or ecdysone-inducible promoter systems. Other production methods involve replacing the toxic VSV-G protein with less toxic glycoproteins.

Lentiviral vectors can also be pseudotyped by various viral surface proteins. The most commonly used is the envelope glycoprotein G of the vesicular stomatitis virus (VSV-G). In addition, various different envelope glycoproteins such as those from gamma-retroviruses (e.g. feline endogenous retrovirus RD114 env, modified gibbon ape leukaemia virus GalV, moloney murine leukaemia virus MLV), alphaviruses or baculoviruses had also been shown to pseudotype lentiviral vectors.

Pseudotyping broadens the transduction range of lentiviruses, and long-term transgene expression has been obtained in many different cells and tissues (Delenda, 2004). Pseudotyping also strengthens fragile lentiviruses and enables concentration to high titers by ultracentrifugation.

Baculoviruses possess several advantages for gene delivery applications. They have a large insert capacity (>100 kb) and are capable of transducing most mammalian cell lines, even in large-scale suspension cell cultures in serum-free conditions (Scott et al., 2007). In addition, baculoviruses are easy to produce in large-scale and high titers, and they present few safety problems as they are not able to replication in mammalian cells. Cytotoxicity is very rarely detected, even with high Multiplicity of Infection (MOI).

Baculoviruses have been used for a large-scale protein production in insect cells and for the production of viral-like particles (VLP), such as hepatitis VLP. Intact viruses have also been produced using hybrid baculoviruses. Baculoviruses-mediated production of recombinant influenza viruses, adenoviruses (Cheshenko et al, 2001) and AAV (Auang et al, 2007) in mammalian cells has also been described.

SUMMARY OF THE INVENTION

According to the present invention, a method of generating a lentivirus vector, comprises cloning each of a lentivirus transfer construct, gag, pol, an envelope protein and rev respectively into the same or different baculoviruses, and transducing a producer cell with the or each baculovirus.

DESCRIPTION OF THE DRAWINGS

The following drawings illustrate embodiments of the inventions.

DESCRIPTION OF THE PREFERRED EMBODIMENTS

To perform the method of the invention, the baculovirus(es) must comprise a lentivirus transfer construct, gag, pol, a suitable envelope protein and rev.

The term "lentivirus transfer construct" will be known to those skilled in the art. A lentivirus transfer construct is a source of lentiviral RNA genome/lentiviral vector RNA and transgene cassette. One example of a lentivirus transfer construct is LV1-GFP. Methods for producing lentivirus transfer constructs will also be known to those skilled in the art.

The term "envelope protein" will be known to those skilled in the art. An envelope protein is a protein that protects the nucleic acid of a virus. An example of envelope protein suitable for use, in the invention is VSV-G.

The term "producer cell" will be known to those skilled in the art. Examples of producer cells suitable for use in the invention are 293T. HepG2, CHO, BHK, Sf9, Sf21, 293, BTI-Tn 5 B 1-4, COS, NIH/3T3, Vero, NSO or PerC6 cells. The produced cells may then be cultured as adherent or in suspension.

Preferably. All the elements needed for the production of functional lentiviruses according to the invention are cloned into three different baculoviruses. More preferable, they are cloned into two different baculoviruses, and most preferably, they are cloned into one single baculovirus. This may be achieved by combining the features of BAC-transfer, BAC-gag-pol, BAC-VSVg and BAC-rev into a single baculovirus.

Four recombinant baculoviruses BAC-transfer, BAC-gag-pol, BAC-VSVg and BAC-rev, derived from *autographa californica* multicapsid nucleopolyhedrovirus (AcMNPV) have been constructed. They encode all the elements needed for lentivirus vector generation in mammalian cells. By transducing 293T cells with these baculoviruses, a functional lentivirus has been produced.

Baculovirus technology is an attractive option for scalable virus production due to ease of production, concentration of baculoviruses, efficient transduction of suspension mammalian cells in serum-free conditions and safety. The lentiviral vector may also be produced with the baculovirus encoding or displaying viral protein rev, tat, net, vit or vpu, by, but are not limited to, fusing the viral protein to a baculovirus protein. The baculovirus protein may be the major envelope protein gp64 or the capsid proteins, vp39 and p24.

The resulting lentiviruses may be pseudotyped with heterologous protein or other ligands, such as VSV-g, gp64, avidin, streptavidin or biotin.

The following Example illustrates the invention.

Materials and Methods

Cloning of Plasmids for the Production of Baculoviruses

Figure 1:
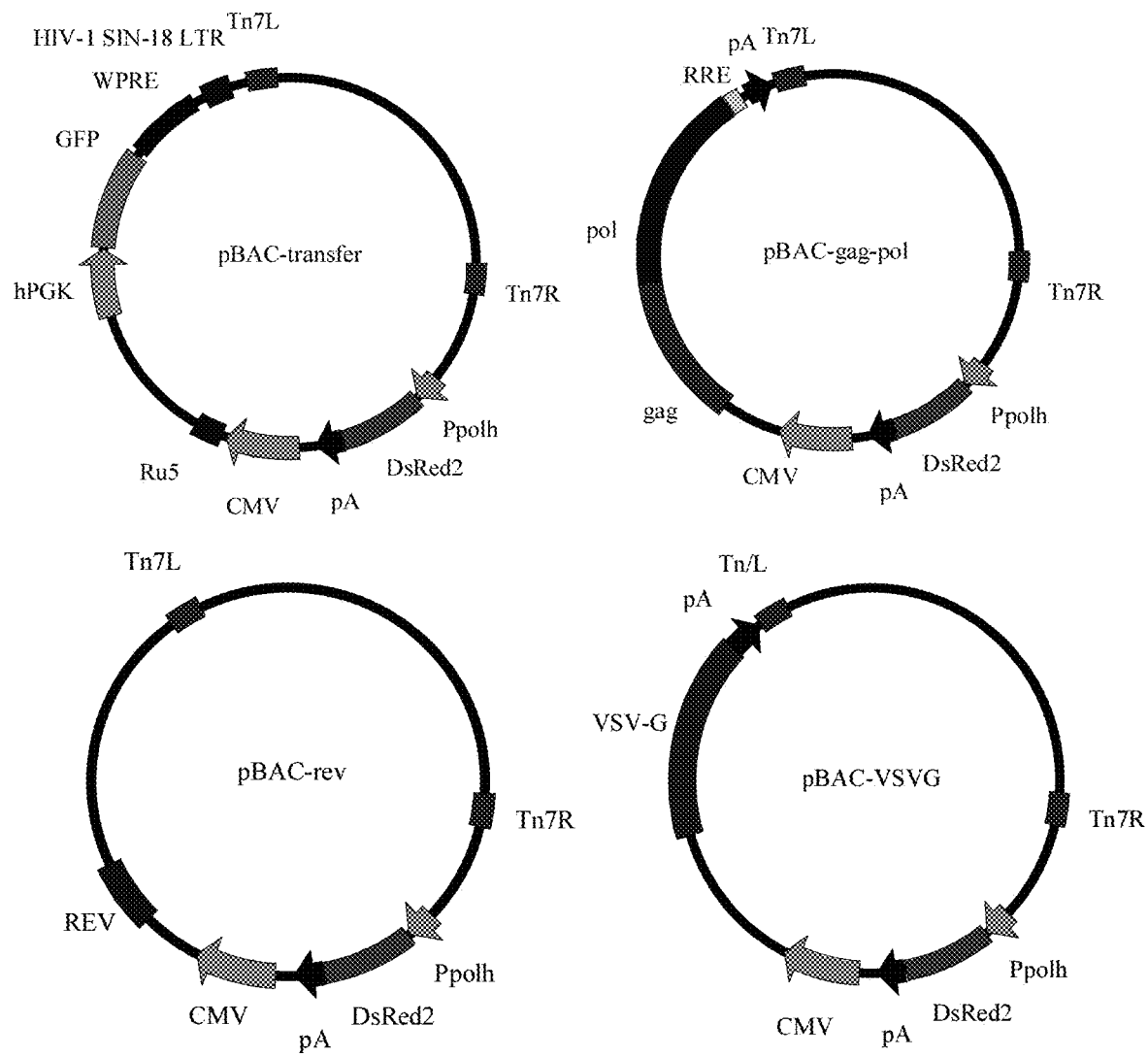
FIG. 1 is a schematic diagram and shows cloned baculovirus donor plasmids, BAC-transfer, BAC-gag-pol, BAC-VSVg and BAC-rev.
Figure 2:
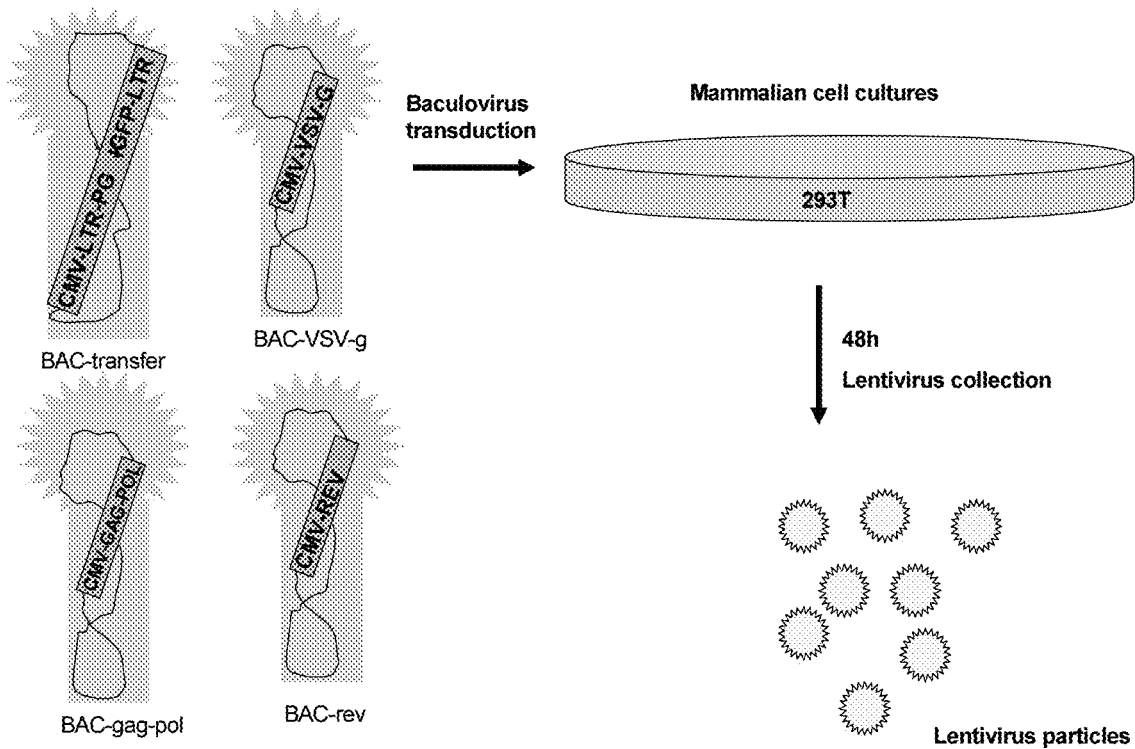
FIG. 2 is schematic diagram of baculovirus-mediated lentivirus production.

All the necessary elements for the production of $3^{rd}$ generation lentiviral vectors in mammalian cells were subcloned into baculovirus donor vector pFastBac1 to construct four recombinant baculoviruses, BAC-transfer, BAC-gag-pol, BAC-VSVg and BAC-rev, derived from *Autographa califomica* multicapsid nucleopolyhedrovirus (AcMNPV) (FIG. 1). First, a polylinker containing multiple cloning sites (Pm/I/NheI/PstII/SalI/AflII/PacI/SpeI/MluI/PmeI/EcoRI/ApaI/SwaI/AscI) was cloned into the unique AvrII site of pFastBac1. The sequence of the polylinker was 5'CACGTG-GCTAGCCTGCAGGTCGACCTTAAGTTAAT-TAAACTAGTACGCGTGTTTAAACGAATTCGGGC-CCATTTAAATGGCGCGCC-3' (SEQ ID No: 1). The donor vector also contained the red fluorescent protein maker gene (DsRed) under the control of a polyhedron promoter for convenient baculovirus titer determination.

To generate a third-generation self-inactivating lentivirus transfer construct, (LV1-GFP) ΔNGFP from plasmid LV-hPGK-ΔNGFP-WPRE-SIN (Makinen, 2006) was replaced by GFP. In this construct, the GFP marker gene is driven by the phosphoglycerate kinase (PGK) promoter. The pBAC-transfer vector was constructed by subcloning the relevant sequence from LV1-GFP into the pFastBac1 donor vector polylinker in two stages. To clone the first part of the sequence, LV1-GFP was digested with BsrBI and AscI and subcloned into SwaI/AscI-site of the donor vector polylinker. The second part of the sequence was cloned by digesting LV1-GFP with AscI and AvrII and inserting the fragment into the AscI and AvrII sites of the modified pFastBac1-plasmid.

The packaging construct (pBAC-gag-pol) expressing gag and poi driven by CMV promoter was derived from the plasmid pMFLg/pRRE (Follenzi and Naldini, 2002) by ApaLI digestion and subcloned into the SmlI-site of the donor vector. Prior to ligation ApaLI ends were blunted with T4 DNA Polymerase (Finnzymes, Helsinki, Finland).

The VSV-G envelope construct from the plasmid pCMV-VSVG was subcloned into the pFastBac1 vector in two stages. First, pCMV-VSVG was digested with Nofl and blunted using T4 DNA Polymerase prior to digestion with EcoRI. This fragment was subcloned to the Sm/I/EcoRI-site of the polylinker. The second part of the sequence was digested from pCMV-VSVG with EcoRI and subcloned into the polylinker EcoRI site.

Rev cDNA was obtained by polymerase chain reaction (PCR) from the plasmid pRSV-REV (Dull et al, 1998) using forward and reverse primers. The forward primer is 5' CGAAG GAATTCGTCGCCACCATGGCAGGAAGAAGCGGA-3' (SEQ ID No: 2). The sequence for nucleotides 1-18 of the rev gene is in bold, the Kozak concensus sequence is in italic, and the EcoRI site underlined. The reverse primer is 5' AGCTA GCTAGCGTATTCTCCTGACTCCAATATTGT-3' (SEQ ID No:3). The sequence for nucleotides 349-325 of the rev gene is in bold and the NheI site is underlined. The amplified PCR product was digested with EcoRI and NheI, purified using a Wizard Clean up kit) Promega, Madison, Wis., USA), and subcloned into the EcoRI/NheI-site of the pFastBac1 polylinker to form pBAC-rev. Rev cDNA was under the control of the CMV promoter which was previously subcloned as a NruI/EcoRI fragment from the pcDNA3 vector (Invitrogen) into the SwaI/EcoRI-site of the pFastBac1 polylinker.

Production of Lentiviruses 293T cells were plated 24 h before transduction. Cells were cultured in Dulbecco's Modified Eagles Medium (DMEM) or RPMI 1640 both supplemented with 10% fetal bovine serum (FBS). Transduction was performed with varying multiplicity of infection (MOI) between 50 and 1000 pfu per cell in either serum-free or serum supplemented DMEM or RPMI. After 4 h incubation in serum-free medium or 18 h in serum supplemented DMEM or RPMI at 37° C. of the cells were washed and medium was changed. The cell supernatant containing lentivirus was collected 48 h post transduction and centrifuged at 1500 rpm for 10 min at room temperature.

As controls, batches were made where each of the three baculoviruses were missing (BAC-gag-pol, BAC-Rev or BAC-VSVg). Lentiviruses were also prepared by conventional four plasmid transient transfection method in 293T cells (Follenzi and Naldini, 2002). To improve the attachment of the cells to the bottom of the plates, the plates were coated with poly-L-lysine, according to the manufacturer's instructions.

Titering of Lentiviruses

Transforming units of lentiviruses (TU/ml) were determined by analyzing the number of virus particles able to transduce HeLa cells. On day one Hela cells were seeded in 6-well plates at $1 \times 10^5$ or in 96-well plates at $5 \times 10^3$ cells per well. The lentivirus transduction was carried out on day two with serial dilution. On day five the cells were visualized with fluorescent microscopy and analyzed by flow cytometry to reveal the percentage of cells which were transduced by GFP expressing lentiviruses. Titers were calculated as described in Follenzi and Naldini, 2002.

Long Term Expression of Transgene

HeLa cells ($5\times10^3$) were seeded on the 96 well plates, transduced next day with baculovirus-produced lentiviruses and cells were cultured up to 6 weeks. GFP expression was monitored weekly by flow cytometer. As an additional control, Hela cells were also transduced with baculovirus BAC-transfer expressing GFP and the expression was monitored in a similar way.

Determination of p24 Concentration

The amount of lentiviral capsid protein p24 (pg/ml) was determined by p24 ELISA kit (NEN™ Life Science Products HIV-1 p24 ELISA). Testing of the replication competent lentiviruses (RCL) was done by p24 ELISA determination from the cell culture supernatants. HeLa cells were transduced with lentivirus and the transduction efficiency was monitored by flow cytometer. Cells were culture for four weeks, supernatants was measured repeatedly as a marker of RCL. This was further confirmed by transducing naive HeLa cells with collected supernatants and GFP expression was monitored by fluorescent microscopy and flow cytometer.

Statistical Analyses

Statistical analyses were performed by GraphPadPrism 4 (GraphPad Software Inc., San Diego, Calif., USA).

Results

Construction of Baculoviruses

The key $3^{rd}$ generation elements were cloned in four baculoviruses. The baculovirus plasmid constructs were verified by restriction analysis and four baculoviruses were generated in insect cells. To monitor consistency of the baculovirus production, immunoblot analysis was conducted on each batch, with anti-gp64 against major envelope protein of baculovirus. End point titer determination (IU/ml) for concentrated baculoviruses was done in insect cells. High titers ($>10^{10}$ IU/ml) were measured for all produced viruses and used to control MOI in lentivirus production.

Production of Lentiviruses

Lentiviruses were produced by transduction of 293T cells with four baculoviruses. Transduction was performed using different mediums and incubation times. The transduction efficacy was monitored 20 h after the transduction by fluorescent microscopy. Lentivirus containing supernatants were collected 48 h after the transduction and titers were determined in HeLa cells as transducing units (TU/ml).

Four baculoviruses at MOI 500 each yielded lentivirus titers with an average of $6.0\times10^5$ TU/ml when transduction was performed 4 h in serum-free conditions. Baculovirus concentration at MOI 750 produced higher lentivirus titers with an average of $1.2\times10^6$ TU/ml. A decrease in titer was detected when higher baculovirus concentrations (four baculoviruses at MOI 1000 each) were used. Four baculoviruses at MOI 250 yielded the highest titers with an average of $2.5\times10^6$ TU/ml when baculovirus transduction was performed over night. When RPMI medium was used in transduction, the highest titers were an average of $5.9\times10^5$ TU/ml already at MOI 50. The titers are comparable to those produced with conventional four plasmid transduction method (Follenzi and Naldini, 2002).

The different ration of plasmids can influence titers in plasmid transfection. When the same ratio of baculoviruses as is commonly used with plasmids were used, the lentivirus titers were 0.64 fold lower than expected. BAC-transfer virus was also doubled, to see if higher lentivirus titers could be obtained. However, there was no significant difference in the tiers compared to the production with similar doses of baculoviruses. Titers obtained with the doubled amount of the BAC-transfer were at on an average of $1.4\times10^6$ TU/ml.

As negative controls, lentivirus production was performed, omitting one of the baculoviruses (BAC-gag-pol, BAC-Rev or BAC-VSVg) at a time. Collected mediums were used to transduce HeLa cells and the number of GFP positive cells (5) was analyzed four days after the transduction by flow cytometer. No GFP positive cells could be determined in these experiments.

A frequently used titration method alongside with a biological titer (TU/ml) of lentiviruses measures p24 concentration (pg/ml) by ELISA. The p24 concentrations in the medium were 191±105 ng/ml which corresponds the value for the representative virus preparations. However, p24 concentration does not separate biologically active particles. To compared infectious particles and p24 ratio, both of these parameters were measured from several preparations produced with different amounts or ratios of baculoviruses. The results showed good TU/p24 ratio.

Characterization of Transgene Expression

Residual baculoviruses in the collected lentivirus medium was evaluated by end point tittering and the titer was 0.1-0.5% from the dose used for 293T cell transduction. To confirm that transgene expression was originated from the produced lentivirus, and not from residual baculovirus, 293T cells were transduced with the BAC-transfer baculovirus only. HeLa cells were then transduced with the medium collected similar way than in lentivirus preparation and GFP positive cells were analysed with flow cytometer four days after transduction. No GFP positive cells could be detected.

Baculovirus vectors do not replicate in vertebrate cells and they cannot integrate into the host genome. Gene expression from these vectors is transient and usually lost in two weeks. However, transgene expression from an integrated lentivirus is relatively stable assuming no silencing of the transgene expression occurs. Baculovirus-produced lentiviruses transduction lead to efficient GFP expression which could still be observed after 43 days post transduction. Expression was also detected by fluorescent microscopy in HeLa cells at day three Baculovirus-mediated GFP expression at MOI 100 and 1000 (18.7±1.9% and 11.5±0.4% at day three, respectively) was lost 17 days after post transduction.

Replication-Competent Lentiviruses

Replication-competent lentiviruses (RCL) were texted by p24 ELISA assay. HeLa cells were transduced with lentivirus containing mediums. Transduction efficiencies were verified by flow cytometer. Cells were cultured for four weeks and concentration of p24 in the supernatant was repeatedly measured. An increasing concentration of p24 would indicate an ongoing viral replication, but no such increase was detected/Mediums collected from transduced HeLa cells after 2.5 weeks were further used to transduce naive HeLa cells but no GFP expression was detected neither with fluorescent microscopy nor flow cytometer.

In summary, successful generation of functional lentiviruses using hybrid baculoviruses has been demonstrated. Lentivirus titers produced by baculoviruses were comparable to those produced using the conventional four plasmid transfection method. Good lentivirus tiers were achieved when optimal dose of baculoviruses and extended transduction time was used. A decrease in lentivirus titers and cell death was observed when high doses of baculoviruses were used. This may be due to the VSV-G toxicity to production cells. No problems were observed when the VSV-G expressing baculovirus was omitted, keeping the total number of baculovirus particles constant. By replacing the DMEM medium with RPMI1640, the lowest baculovirus dose (MOI 50) resulted in the best lentivirus titers. This is in line with the fact that the transduction medium affects baculovirus-mediated gene expression in vertebrate cells. To confirm the functionality of the generated lentiviruses, HeLa cells were transduced and sustained GFP expression was observed for 6 weeks. However, with the control baculovirus the GFP expression was lost in 17 days. If lentivirus generation was performed by omitting either BAC-gag-pol, BAC-Rev or BAC-VSVg, no lentivirus was produced.

Although baculoviruses are safe, contamination of the lentivirus preparation with baculoviruses is not desirable. The amount of residual baculoviruses in the lentivirus preparations was only 0.1-0.5% of the baculovirus dose used in the simple lentivirus production protocol in which the 293T cells were washed only once after baculovirus transduction. The residual baculovirus may be further reduced by simply adding extra washing step(s) or using adequate down-stream purification schema.

One of the major concerns associated with the use of lentiviral vectors is the probability of generating pathogenic human viruses. To avoid this, the lentivirus genome was separated into four different production plasmids in order to minimize the risk of RCL formation by recombination. No RCL was detected fin the baculovirus-generated lentivirus preparations. p24 levels were not increased after prolonged cultures and no GFP expression was detected in 2.5 weeks after transduction.

The scalability of virus production for clinical studies remains difficult in adherent cells. Thus, adaptation of lentivirus production to suspension cell cultures would be advantageous. Preliminary results in suspension adapted HEK293 cells in serum-free conditions showed very efficient baculovirus transduction efficacy (95.1% GFP positive cells).

REFERENCES

Delenda, 2004. *J Gene Med.* 6 Suppl 1: S125-5138.
Lu, et al. *J. Gene Med.* 6, 963-973 (2004).
Follenzi, & Naldini *Methods Enzymol.* 346, 454-465 (2002).
Ni, et al. *J. Gene Med.* 7, 818-834 (2005).
Cheskenko, et al, *Gene Ther.* 8, 846-854 (2001).
Makinen, et al. *J. Gene Med.* 8, 433-441 (2006).
Dull, et al. *J. Virol.* 72, 8463-8471 (1998).

We claim:

1. A DNA having a sequence selected from SEQ ID No: 1; SEQ ID No: 2; or SEQ ID No: 3.

2. The DNA of claim 1, the DNA having the sequence of SEQ ID No: 1.

3. The DNA of claim 1, the DNA having the sequence of SEQ ID No: 2.

4. The DNA of claim 1, the DNA having the sequence of SEQ ID No: 3.

\* \* \* \* \*

SEQUENCE LISTING

```
<160> NUMBER OF SEQ ID NOS: 3

<210> SEQ ID NO 1
<211> LENGTH: 86
<212> TYPE: DNA
<213> ORGANISM: Artificial Sequence
<220> FEATURE:
<223> OTHER INFORMATION: Linker. Sequence is synthesized.

<400> SEQUENCE: 1
cacgtggcta gcctgcaggt cgaccttaag ttaattaaac tagtacgcgt gtttaaacga    60
attcgggccc atttaaatgg cgcgcc                                        86

<210> SEQ ID NO 2
<211> LENGTH: 38
<212> TYPE: DNA
<213> ORGANISM: Artificial Sequence
<220> FEATURE:
<223> OTHER INFORMATION: Primer. Sequence is synthesized.

<400> SEQUENCE: 2
cgaaggaatt cgtcgccacc atggcaggaa gaagcgga                           38

<210> SEQ ID NO 3
<211> LENGTH: 35
<212> TYPE: DNA
<213> ORGANISM: Artificial Sequence
<220> FEATURE:
<223> OTHER INFORMATION: Primer. Sequence is synthesized.

<400> SEQUENCE: 3
agctagctag cgtattctcc tgactccaat attgt                              35
```